United States Patent [19]

Haynes

[11] 4,165,484

[45] Aug. 21, 1979

[54] PARTICLE COUNTING APPARATUS UTILIZING VARIOUS FLUID RESISTORS TO MAINTAIN PROPER PRESSURE DIFFERENTIALS

[75] Inventor: John L. Haynes, Redwood City, Calif.

[73] Assignee: Becton, Dickinson and Company, Rutherford, N.J.

[21] Appl. No.: 780,402

[22] Filed: Mar. 23, 1977

[51] Int. Cl.² ................... G01N 27/00; A61B 5/00
[52] U.S. Cl. .................. 324/71 CP; 235/92 PC; 364/555; 128/1 R
[58] Field of Search .......... 324/71 CP; 73/432 PS; 235/92 PC; 364/555; 356/102; 128/2 G

[56] References Cited

U.S. PATENT DOCUMENTS

| 4,014,611 | 3/1977 | Simpson et al. | 324/71 CP |
| 4,070,617 | 1/1978 | Rachel et al. | 324/71 CP |

OTHER PUBLICATIONS

Spielman et al., Improving Resolution in Coulter Counting; Journal of Colloid & Interface Science; vol. 26, pp. 175–182 (1968).
Byerly et al., Machine For Rapidly Counting Etc.; Rev. of Scien. Inst., vol. 46, No. 5, May 1975, pp. 517–522.
Thom, Reinhard; Vergleichende Untersuchuengen zur Electronischen Zellvolumen-Analyse; AEG Telefunken Pub., N1/EP/1968.

Primary Examiner—Robert J. Corcoran
Attorney, Agent, or Firm—Flehr, Hohbach, Test, Albritton & Herbert

[57] ABSTRACT

Apparatus and a method therefor for counting platelets and red blood cells in a whole blood sample includes an aperture type transducer having front sheath and back sheath flows but also including various fluid resistors to maintan proper pressure differentials and which are driven from a common air supply. The whole blood sample is injected through the aperture by use of a small bore tube also driven by the common air supply.

34 Claims, 14 Drawing Figures

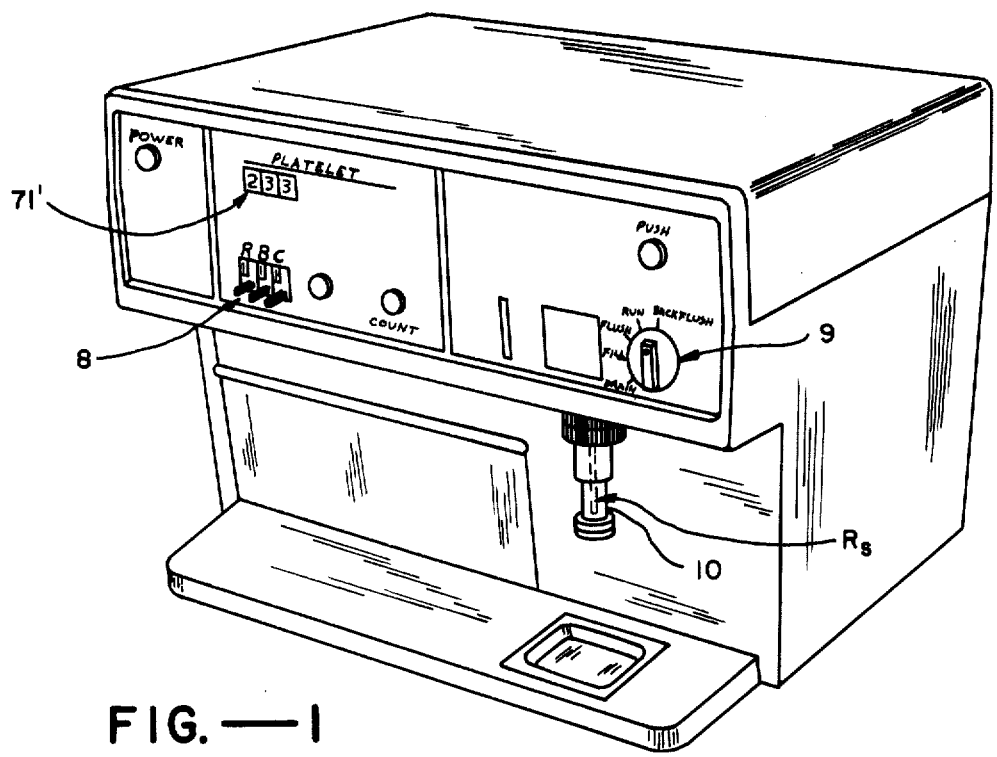
FIG.—1
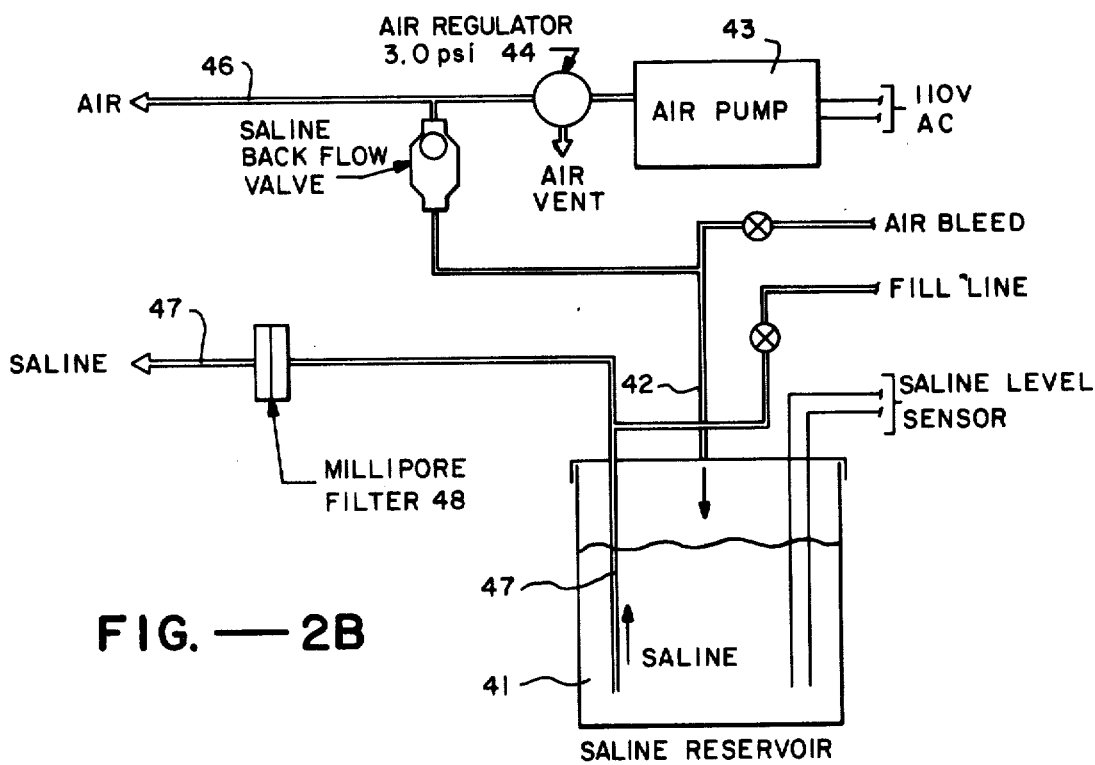
FIG.—2B

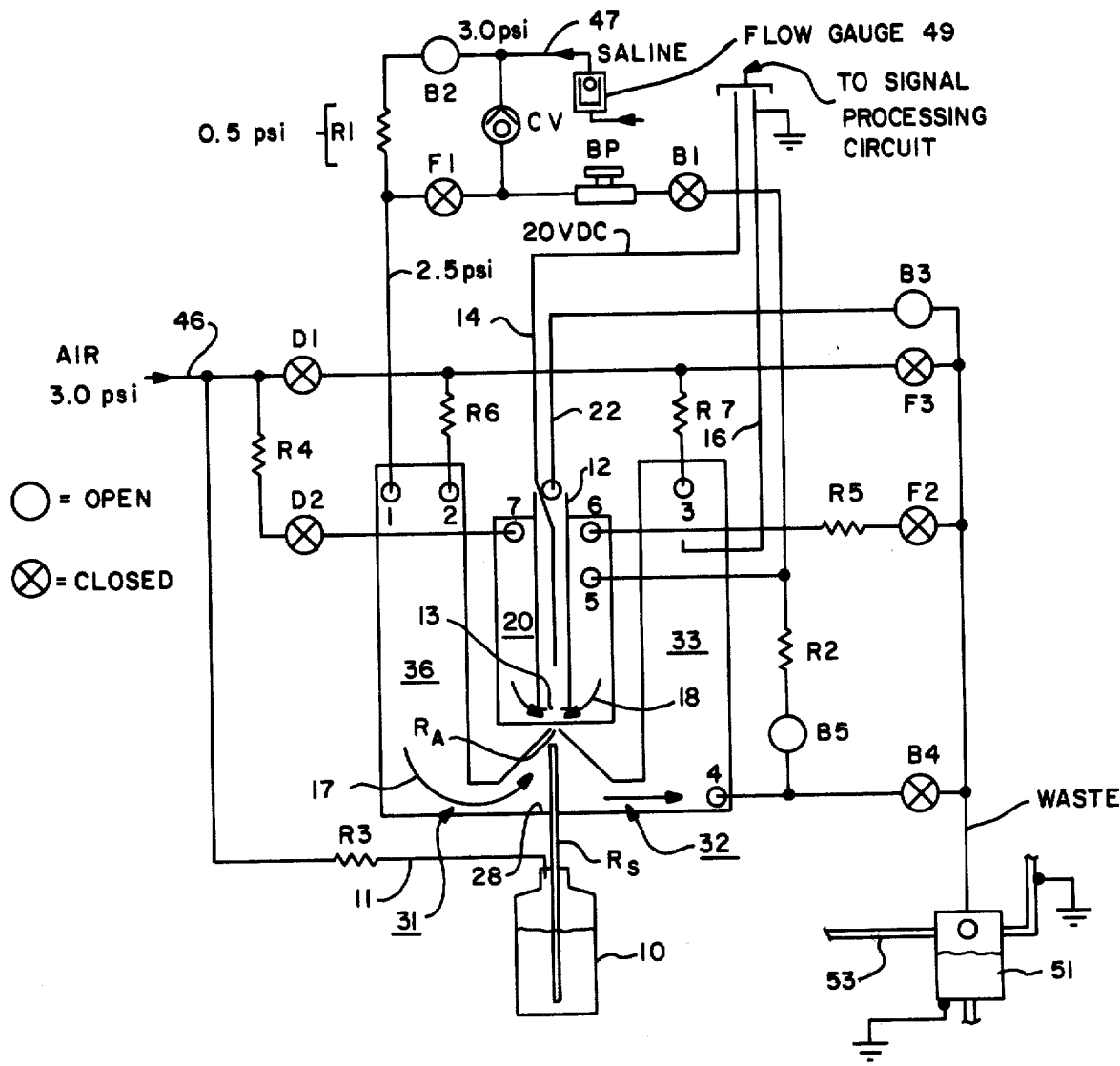
FIG.—2A
|  | B1 | B2 | B3 | B4 | B5 | F1 | F2 | F3 | D1 | D2 |
|---|---|---|---|---|---|---|---|---|---|---|
| DRAIN | X | X | O | O | X | X | X | X | O | O |
| FILL | O | — | X | X | X | O | O | O | X | X |
| FLUSH | O | — | O | O | X | O | X | X | X | X |
| RUN | X | O | O | X | O | X | X | X | X | X |
| B. FLUSH | O | X | X | O | O | X | X | X | X | X |
O = OPEN
X = CLOSED
FIG.—2C

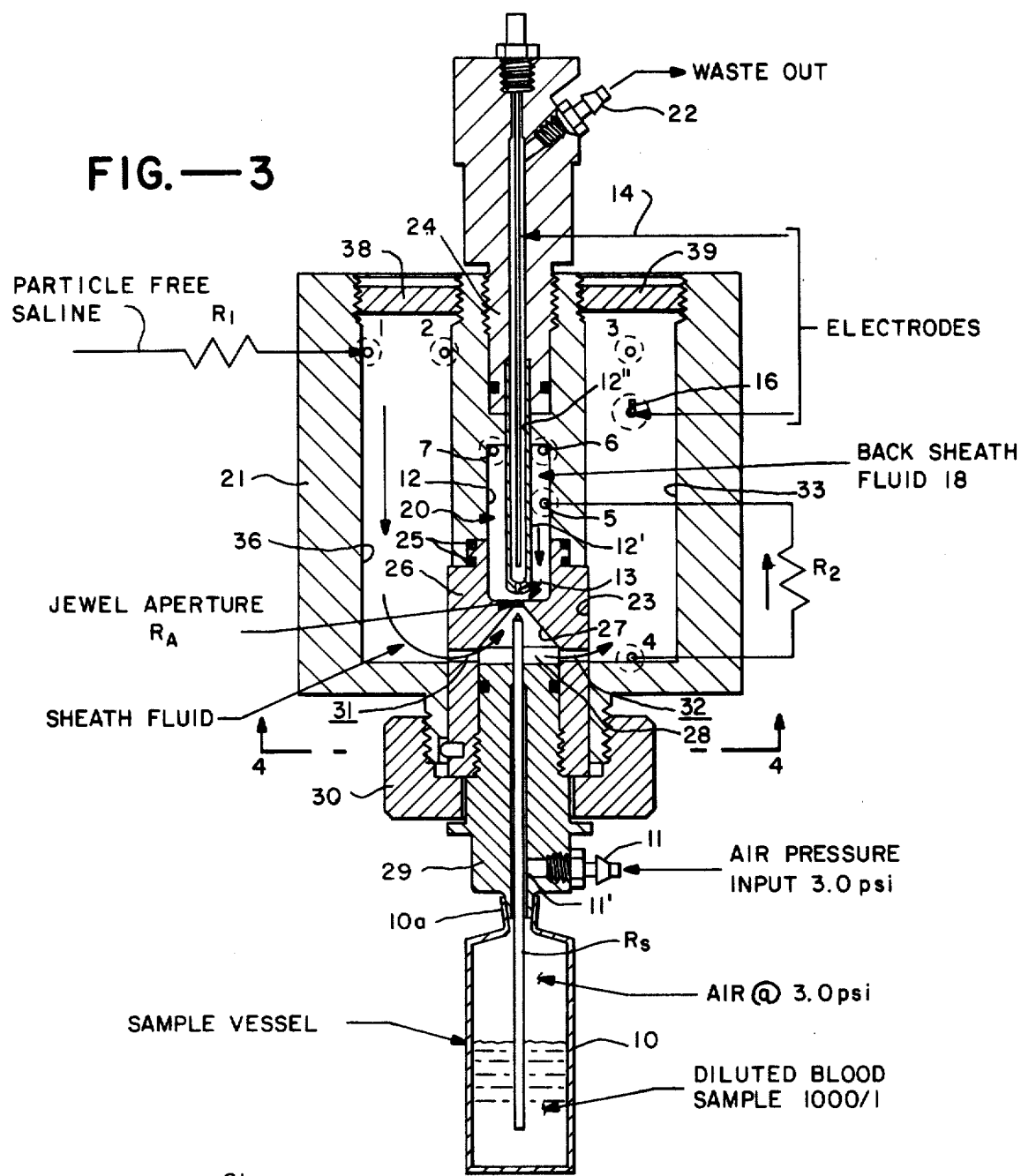
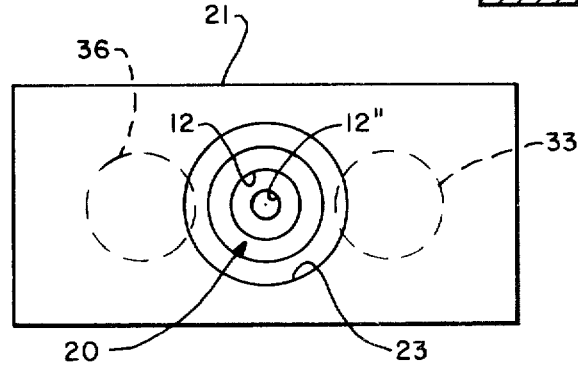
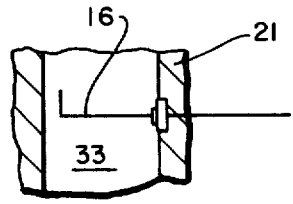

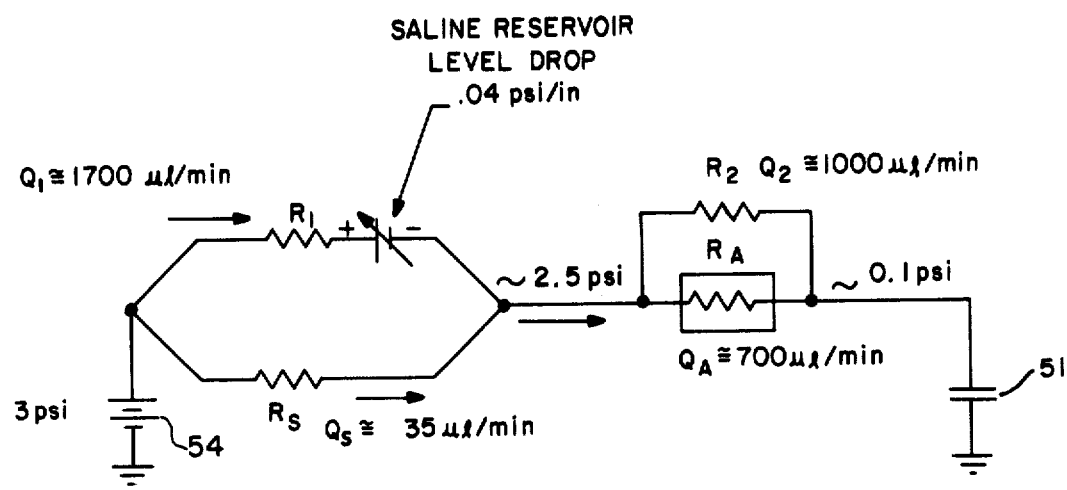
FIG.—5
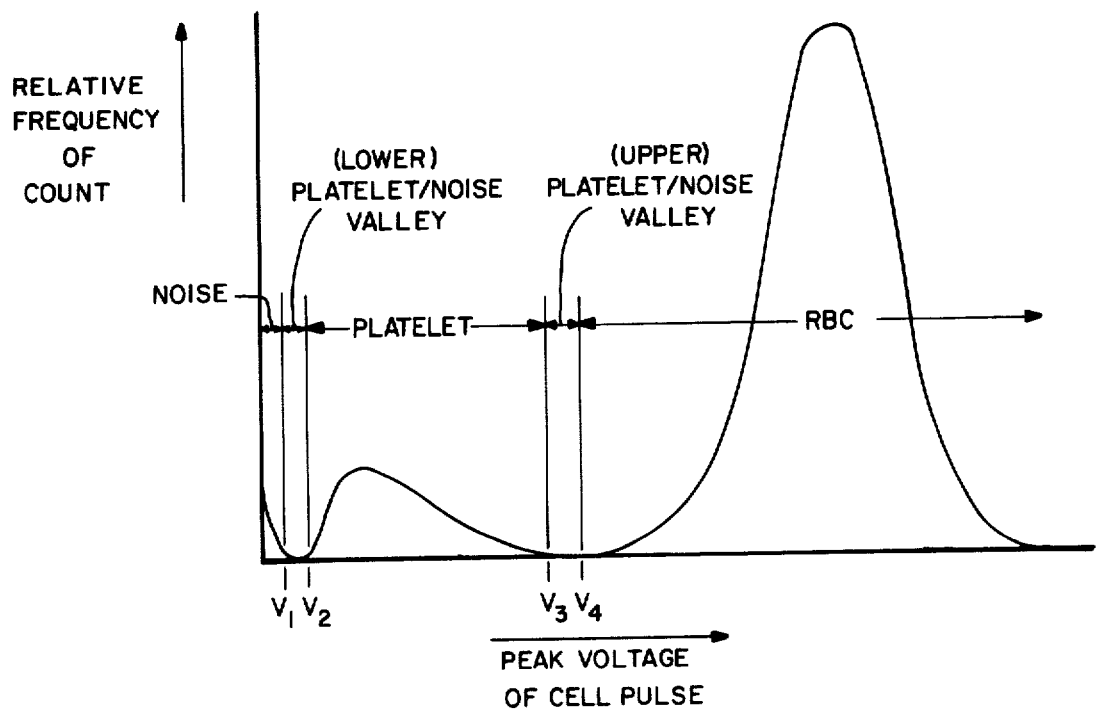
FIG.—8

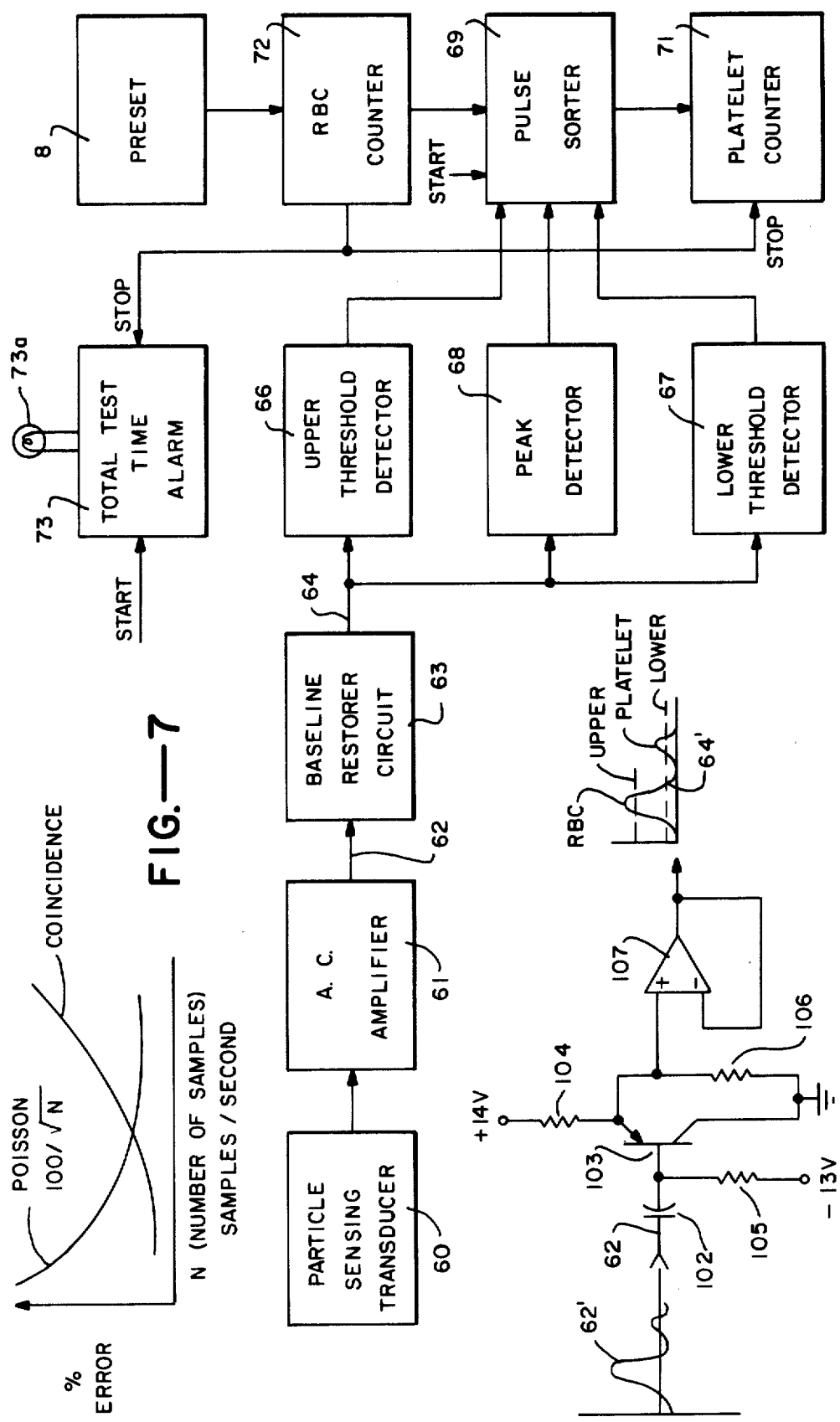
FIG.—6
FIG.—6A
FIG.—7

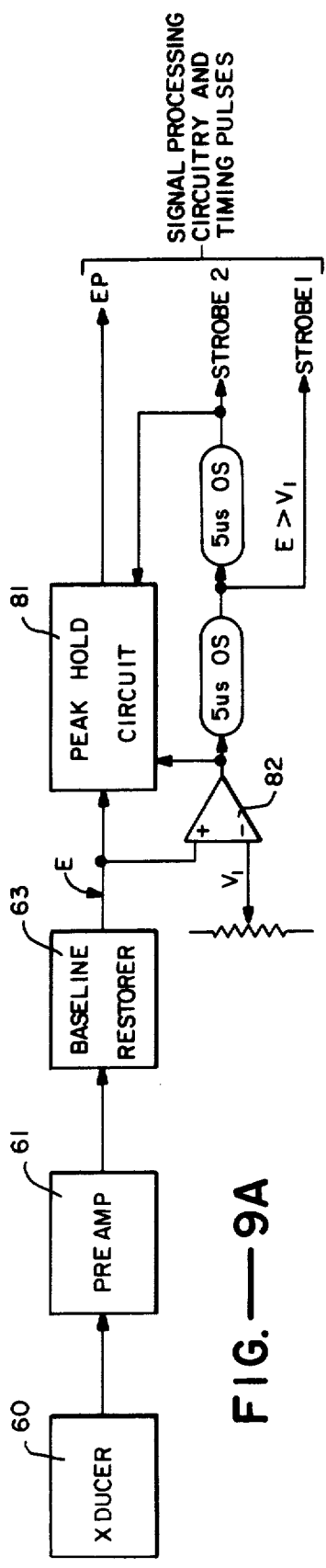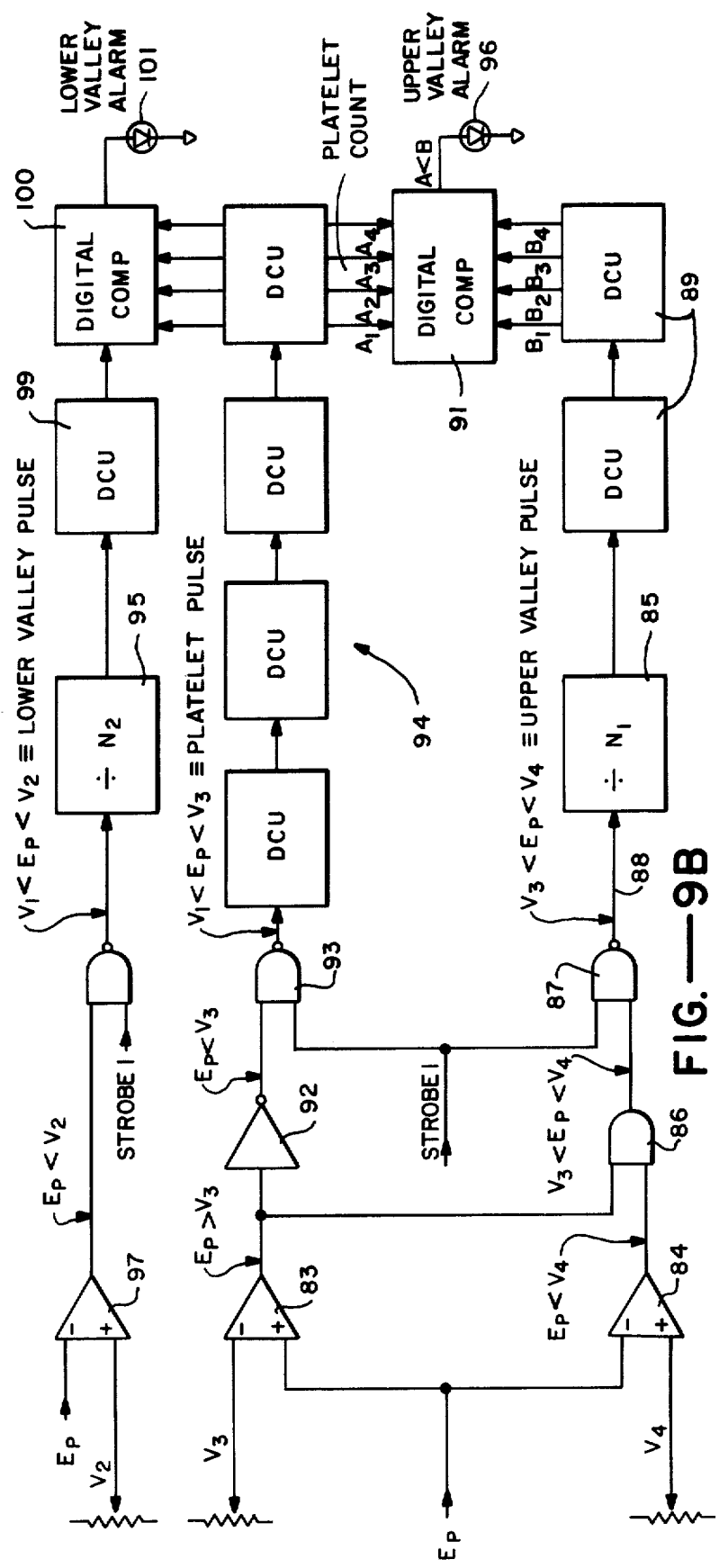

PARTICLE COUNTING APPARATUS UTILIZING VARIOUS FLUID RESISTORS TO MAINTAIN PROPER PRESSURE DIFFERENTIALS

BACKGROUND OF THE INVENTION

The present invention relates to an apparatus for counting particles in a liquid suspension and method therefor and more specifically to apparatus for counting both red blood cells and platelets in whole blood.

In a copending application titled "Particle-Density Measuring System" in the names of the present inventor and Bernard A. Shoor, and filed Nov. 4, 1976, Ser. No. 738,896 now abandoned, and continuation-in-part application Ser. No. 832,893, now U.S. Pat. No. 4,110,604 a technique is disclosed for determining the number of platelets per unit volume of a blood sample by the use of a ratio method. Specifically, red blood cells are counted simultaneously in the same sample with platelets to thus provide a ratio of platelets counted to red blood cells counted. Then if the red blood cell density is known, the platelet density is immediately available.

The general concept of electronically counting different types or sizes of particles has been suggested in a Coulter U.S. Pat. No. 2,656,508. However, because of the quantum difference in both size and volume between red blood cells and platelets there is great difficulty in obtaining an accurate platelet count. For example, as stated in an article entitled "Electrical Sizing and Counting of Platelets in Whole Blood" by J. Schulz and R. Thom, *Medical and Biological Engineering*, July 1973 pp. 447-454, on page 448

> "... it is difficult or even impossible to analyse a large and small particle population in the same suspension. This problem arises in many applications and is of special interest if platelets and red cells are to be analysed from whole blood.
> To overcome these disadvantages, the particles should be injected into the centre of the orifice only, and those particles outside the hole should be kept out of the current density field."

FIG. 1 of the Thom Article on page 447 shows the use of a jet capillary with the use of a front sheath for increased resolution. He further states on page 448 regarding the jet tube > To obtain stable conditions for the hydrodynamic focusing process and a constant diameter of the central particle-suspension stream, no pressure is applied to the jet capillary tube.

A Thom U.S. Pat. No. 3,810,010 shows a capillary tube with the use of a front sheath apparently similar to the Thom article. The Thom article also cites on its page 454 a German Thom article dated 1972 entitled "Vergleichende Untersuchungen zur Elektronischen Zellvolumenanalyse" *AEG Telefunken Publ.* N1/EP/1698. The German Thom in FIG. 10 shows counting apparatus which has both front sheath and back sheath flows and apparently uses a jet capillary similar to the *Medical and Biological Engineering* Thom article. FIG. 10 shows that the pressure, $P_3$, of the jet capillary is equivalent to the front sheath pressure, $P_2$, which is much greater than the back sheath pressure, $P_1$ which in turn is greater than the waste tube pressure, $P_0$. In addition, the drawing appears to show that the pressure $P_1$ is derived from $P_2$ or $P_3$ by a pressure reduction constriction.

An article by Spielman and Goren in the *Journal of Colloid Interface Science* 26, 175-182 (1968) entitled "Improving Resolution in Coulter Counting by Hydrodynamic Focusing" discloses the use of a front sheath for improved resolution.

Finally a cell sorter product manufactured and sold by Becton Dickinson Corporation under Model FACS, (the assignee of the present invention) uses a small bore tube as a fluid resistor connected in line with larger bore tubing for driving a sample fluid through an aperture which is at the apex of a conical structure into which the larger tubing extends. The cell sorter operates on the principle of dividing the fluid into droplets by means of the aperture and vibration and then sorting the droplets.

OBJECTS AND SUMMARY OF THE INVENTION

It is a general object of the present invention to provide an improved apparatus and method for counting particles in a liquid suspension and method therefor.

In accordance with the above object there is provided an apparatus for counting particles in a liquid suspension. Particle sensing means include a sensing zone. There is a source of particle free liquid. A unitary small bore tube has an end which is juxtaposed with the sensing zone. Under a predetermined pressure the suspension is forced through the tube into the sensing zone. Hydrodynamic focusing means direct a first flow of the particle free liquid through the sensing zone in cooperation with the liquid suspension.

Finally, there are disclosed and claimed a method of dilution of a blood sample, apparatus for providing a high and repeatable sampling rate, and apparatus for providing alarms indicating a defect in the counting procedure.

BRIEF DESCRIPTION OF THE DRAWINGS

FIG. 1 is a perspective view of the housing of the apparatus embodying the present invention;

FIGS. 2A and 2B are schematic diagrams of apparatus embodying the present invention;

FIG. 2C is a valve operating table for FIG. 2B;

FIG. 3 is a cross-sectional view of a portion of the apparatus of FIG. 2A;

FIG. 3A is a cross-sectional view of a portion of FIG. 3 the cross-section being rotated 90° from FIG. 4;

FIG. 4 is a simplified cross-sectional view taken along the line 4—4 of FIG. 3;

FIG. 5 is an equivalent circuit of a portion of FIG. 2A;

FIG. 6 is a block diagram of a signal processing circuit;

FIG. 6A is a detailed circuit of a portion of FIG. 6;

FIG. 7 is a set of curves useful in understanding the invention;

FIG. 8 is a typical whole blood cell distribution curve; and

FIGS. 9A and 9B are block diagrams illustrating an alarm circuit of the present invention.

DETAILED DESCRIPTION OF THE PREFERRED EMBODIMENT

FIG. 1 is a perspective view of the laboratory instrument showing a vessel 10 containing a diluted whole blood sample whose platelets are to be counted. A tube $R_S$ extends toward the bottom of vessel 10 for transferring the sample to the instrument.

Different modes of operation are provided by a rotary switch 9; namely, DRAIN, FILL, FLUSH, RUN and BACK FLUSH. Finally, a set of thumb wheel switches 8 allows for entry of a known red blood cell density. Platelet density is then read out at 71'.

Referring to FIG. 2A, vessel 10 contains a sample of whole blood diluted in a ratio of approximately 1,000:1 which is a liquid suspension of particles including red blood cells and platelets. The blood sample is communicated to an aperture $R_A$ by the small bore tube designated $R_S$, one end of the tube being immersed in the sample and the other end being juxtaposed in close proximity with the aperture (e.g. approximately 30 diameters away from the aperture, the diameter of the aperture being the measurement unit). By means of a tube 11 air is injected into the closed vessel 10 with a pressure of 3 psi to provide a driving or motivating force for causing the sample fluid to flow upwards in the tube, $R_S$. The sample is injected through the aperture $R_A$ and into an outlet chamber 12 having an opening 13 juxtaposed with the aperture on the opposite side of it as the end of sample tube $R_S$.

A first electrode 14 is immersed in the outlet chamber 12 and has a dc current applied to it which results in an effective 20 volt dc source of voltage and cooperates with a second electrode 16 in accordance with well-known theory to sense the passage of a particle through the aperture $R_A$ and produce a pulse type signal which is indicative of the passage of the particle as well as its size. For example a platelet pulse will be approximately one tenth the size or magnitude of an average red blood cell pulse. By proper threshold discrimation in a signal processing circuit as described in the above Haynes/Shoor copending application and as shown in simplified form in FIG. 6 the number of platelets and red blood cells can be concurrently counted in the same sample.

In order to provide for improved hydrodynamic focusing of the passage of particles through the aperture $R_A$ and also to eliminate spurious signals, a front sheath fluid as shown by the arrow 17 (and into which the sample is injected) focuses the sample in its passage through the aperture, $R_A$. Generally a "front sheath" may be defined as a particle free fluid used to confine the passage of a particle containing sample through an orifice to a centrally located streamline giving more precise and predictable measurements. It is described in detail in the above Spielman and Goren article but is characterized there as "hydrodynamic focusing". A back sheath fluid flow 18 on the other side of the aperture aids the passage of the sample and immunizes against spurious signals. A "back sheath" is particle free fluid used to confine the passage of a jet emerging from an orifice into an exit tube (termed a "catcher tube" in Coulter U.S. Pat. No. Re. 28,588). This prevents eddy currents and resultant recirculation of sample particles in the region downstream of the orifice which otherwise tend to cause errors in the particle count. The aperture and associated means for facilitating the back sheath and front sheath flows of FIG. 2B is shown in greatly enlarged detail in FIGS. 3 and 4.

In general the particle counter is built around a rectangular block 21 of clear plastic of the polycarbonate type (e.g. LEXAN, a trademark). The transparency of the main building block of the particle counter allows the user to see all important fluid paths and the aperture $R_A$, to check for proper operation e.g., clogging or bubbles. The central portion of block 21 includes a central cylindrical cavity 20 having at its upper portion an outlet chamber 12 and an enlarged diameter lower portion 23 (see FIG. 4). Chambers 33 and 36 are opposed cylindrical cavities in block 21 which are adjacent to cavity 20 and intersect the enlarged cross-section 23.

Chamber 12 is connected to a waste output line 22 and has a catcher tube 12' with its opening 13 opposite and approximately 25 mils from the jewel orifice or aperture $R_A$. Catcher tube 12' is retained by the necked down portion 12" (see FIG. 4) and by a holder 24 inserted into the top of cavity 20, the holder providing the waste outlet 22.

The enlarged lower portion 23 of cavity 20 has inserted in it the holder assembly 26 for the aperture jewel which contains the jewel at the apex of its conical chamber 27 into which the sample tube $R_S$ extends. Since assembly 26 is retained only by the screw-on cap 30 and the O-rings 25 at its other end it is easily removable to allow cleaning of the aperture jewel. Moreover, because the electrode 16 is conveniently located in chamber 33, no electrical connections need be disconnected.

The base or floor 28 of the cone is formed by a holder 29 for the sample tube $R_S$. Near this floor is a fluid passage 31 which extends through the jewel holder 26 for the total sheath fluid and an opposite juxtaposed passage 32 for the back sheath fluid. Passages 31 and 32 are formed by the intersection of chambers 36 and 33 with cavity 20 as shown in FIG. 4. By means of these juxtaposed fluid passages the floor 28 of the conical receptacle 27 is swept clean of debris. The back sheath fluid as indicated by the arrow, passes through passage 32 into a chamber 33, which contains the electrode 16 (see FIG. 3A), and then exits this chamber through a back flow fluid resistor R2. R2 is connected to chamber 33 by a coupling 4 and connects the back sheath fluid flow to the chamber 12 by a coupling 5. In back sheath fluid chamber 20 couplings 7 and 6 are for filling and flushing purposes.

Sheath fluid enters a settling chamber 36, included in the block 21, by means of an input coupling 1 connected to a fluid resistor R1. The sheath fluid is particle free saline which has an input pressure of 3 pounds per square inch as it enters $R_1$.

Settling chamber 36 and electrode chamber 33 both are sealed at their top portions by plugs 38 and 39. Alternatively they may be automatic gas bleed films which may, for example, consist of CELGARD, a trademarked material of Celanese Corporation. This material passes gas but blocks liquid because its hydrophobic surface is nonwetting.

With the use of the small bore tube $R_S$ extending into conical receptacle 27 clogging of aperture $R_A$ is substantially eliminated. The cooperation of the front sheath fluid and the pressure across $R_S$ with the foregoing are believed to be important in preventing such clogging.

The construction and location of electrodes 14 and 16 result in improved operation for several reasons. With electrode 16 located in fluid chamber 33 (as opposed to a typical location in the sample chamber) no deleterious electrode products can flow through the sensing aperture $R_A$. Secondly, construction is simplified since 30 mil diameter platinum wire is used as opposed to 1 square cm foil. Electrode 16 has a length of approximately one inch and electrode 14 is approximately two inches.

Referring now also to FIGS. 2A and 2B the saline particle free fluid for the front and back sheaths is provided by a saline reservoir 41. The saline is driven at an air pressure of 3 psi by the air line input 42 which is connected to an air pump 43 through an air regulator 44. Regulator 44 is also connected via line 46 to the sample vessel 10 and its air input line 11 through a fluid resistor R3. Holder 29, as shown in FIG. 3, forms a spaced collar around tube $R_S$ and air enters this space through the aperture 11' in the collar. Vessel 10 has an upper sleeve type opening 10a which accurately mates with the end of holder 29. Thus the air is efficiently and easily injected into vessel 10. Moreover, vessel 10 contains an exact volume which has been precisely diluted. Fluid resistor R3 is for the purpose of limiting air flow when vessel 10 is removed for refilling. Flow is limited by the fluid resistor R3, which may be constructed of flexible tubing, for example, SILASTIC or TYGON (both trademarks) which has a nominal inner diameter of 0.015 inches and is five inches in length. The approximate flow will be 200 milliliters per minute of air at 3 psi.

The common source of air 43, 44 is provided for both the saline reservoir 41 and the sample vessel 10 and by means of saline reservoir 41 the same pressure is present on fluid line 47 which extends through a millipore filter 48 and a flow gauge 49 to the fluid resistor R1. Gauge 49 is used for fault sensing purposes since if the normal flow rate (2 ml min) changes substantially there is obviously a malfunction. Valve B2 is indicated as being open, i.e., allowing fluid flow. All valves which have an X in the circle are closed to fluid flow and used for filling and other maintainence purposes as shown in the table of FIG. 2C whose five functions correspond to the rotary switch 9 (FIG. 1).

A second open valve, B5, is in series with fluid resistor R2 to allow passage of the back sheath fluid.

Waste on line 22 passes through the open valve B3 and through a drip isolator 51 (which is well known in the art) and discharges to a waste receptacle (not shown). Thus as shown in FIG. 2C in the RUN condition valves B2, B3 and B5 are open allowing fluid flow. The entire transducer structure, valving and fluid resistors are contained within electromagnetic shield 53 and isolated so that no spurious signals interfere with the signal generated on electrodes 14, 16. Waste line 22 is at a +20 volts dc since the saline fluid is a good conductor to the electrode 14 which is connected to the positive terminal of the supply current. Drip isolator 51 isolates this voltage from the shield or other portions of the structure.

Although air pressure is shown as driving saline reservoir 41 and vessel 10, some other fluid such as a lighter liquid could be used. And also a suitable pressure differential may be alternatively provided by placing a 3 psi vacuum on the outlet of isolator 51 and allowing vessel 10 and reservoir 41 to be exposed to the ambient atmosphere.

FIG. 5 illustrates the fluid resistors and the circulation of both sheath fluid and sample fluid in an equivalent electrical circuit diagram. The 3 psi pressure type driving force is shown as a battery 54. Fluid resistor R1 and the sample tube $R_S$ are connected essentially in parallel to the common source 54 since the 3 psi air source is in effect common as explained. A pressure drop of 0.5 psi is developed across this parallel combination which is essentially provided by the relatively large sheath flow $Q_1$ of approximately 1700 microliters per minute through R1. For the small bore tube $R_S$, $Q_S$ is approximately 35 microliters per minute. Thus the sheath fluid leaving R1 is at a pressure of 2.5 psi, which is the pressure existing in settling chamber 36 and at the end of sample tube $R_S$. Thus as is apparent there is a remaining 2.5 psi pressure drop which occurs across the aperture $R_A$ and the fluid resistor R2, which carries the back sheath fluid and is essentially in parallel with $R_A$. R2 has a fluid flow $Q_2$ of approximately 1,000 microliters per minute at 2.5 psi which is less than the $Q_1$ flow. It is obvious that the difference between $Q_2$ and $Q_1$ is the amount of fluid flow $Q_A$ through the aperture which is 700 microliters per minute at 2.5 psi.

In general the foregoing fluid flows and pressure drops may be analogized to a network problem in Ohm's law where $R_A$ is in parallel with R2 the combination in series with R1 with their "resistive" values being chosen to obtain the desired flows and pressure drops.

The ratio of $Q_A$ to $Q_S$ provides a 20/1 dilution ratio which is in addition to the already 1,000:1 dilution which is present in the sample vessel 10 (FIG. 1).

The relatively high electrical resistance of R2 of approximately 1 megohm insures that the electrical shunting of the aperture $R_A$, which has a resistance of approximately 25 kilohms, is small in order not to affect the magnitude signal output of the electrodes. In addition, the small constant error introduced is easily calibrated out. As indicated in FIG. 5 the ratio of $Q_1$ to $Q_S$ is 34:1; it is believed that this large ratio provides a stable pressure drop for maintaining a relatively constant flow and therefore accurate measurement. The various lengths and diameters and materials of R1, R2, $R_S$ and $R_A$ is given in FIG. 5 to provide the foregoing flows. R1 and R2 are glass capillaries to provide for precise dimensions and fluid resistance.

An alternative connection of R2 is directly to the 3 psi source 54. This would allow the $Q_1$ flow to be reduced to 700 microliters per minute.

The electrical impedance of R1 is also designed to be high enough that is, approximately 0.5 megohms to provide an electrical isolation between the fluid source and the transducer. This allows saline reservoir 41 (FIG. 2B) to be unshielded with the noise currents from the reservoir being shunted to ground at the shield 53. R1 insures that this ground contact has negligible effect on the transducer circuit.

The use of the small bore tube $R_S$ for sample entry facilitates switching samples since one vessel 10 is removed and another easily substituted. Furthermore there is almost no sample carryover into the next measurement since the volume of tube $R_S$ is approximately 1.5 microliters. Moreover even this small amount of sample is eliminated due to the pressure reversal when vessel 10 is removed. In other words, there is a back flow of particle free saline solution. And while a new sample vessel is being installed, a drop of saline solution into the vessel is not harmful since a precise dilution of the sample is not necessary as disclosed below.

Since particle free saline solution is relatively expensive the present invention uses a minimum of such fluid (approximately 2 ml/min). This is principally accomplished by the very close proximity of catcher tube opening 13 (FIG. 3) to $R_A$ (approximately 25 mils). There is high velocity flow but yet low volume since opening 13 may be relatively small.

A single air supply in combination with the technique of driving the sample vessel 10 insures that the relative proportions of fluid flow are to a first approximation independent of air pressure. $R_S$ minimizes changes in sample flow, $Q_S$, which could be caused by changes in pressure between the sample and total sheath fluid which would be caused by changing liquid level in, for example, saline reservoir 41; i.e., 0.04/psi/inch of liquid drop. The variable battery in FIG. 5 in series with R1 simulates this drop.

However changes in the 3 psi driving force along with changes in R1, R2 and $R_4$ will have an effect on $Q_S$. To reduce this sensitivity the saline reservoir 41 may be lowered in elevation several inches with a compensating decrease in R1. For example, a saline reservoir level 13.5 inches lower than the sample elevation is equivalent to increasing the effective battery to 0.5 psi, with R1 equal to zero. $Q_S$ is then independent of changes in the 3 psi driving force or of changes in $R_2$ or $R_4$.

The remaining valving is used to fill, to drain, and to provide sustained reverse pressure on the aperture $R_4$ to clear blockages and sweep away debris as shown by FIG. 2C. The back pressure plunger, BP, indicated between the valves F1 and B1 helps give a high momentary back pressure to force blocking debris out of the aperture. A continuous back pressure of 3 psi then provides a back flow to flush the blocking debris to the waste line 22.

Settling chamber 36, contained with the block 21, for the sheath flow provides for thermal settling to eliminate base line noise caused by nonuniform temperatures, debubbles the incoming saline fluid, and traps the lighter than saline debris such as lint which might otherwise clog the aperture or orifice $R_4$. Millipore filter 48 in saline line 47 also provides debubbling but for small as well as large bubbles; such small bubbles could be mistakenly counted as a particle. Finally as discussed above the routing of the back sheath fluid from passage 31 to passage 32 and thus across the floor of the sensing cone causes the cone to be continuously swept free of any settled debris.

The use of the front sheath fluid for dilution avoids the use of a two step process for dilution of the blood sample which would otherwise have to be done; that is, a 20,000/1 dilution is too large for a single step. Moreover, this dilution is desirable since accuracy of the measurement is increased by reducing the density of red blood cells. The dilution ratio is also maintained relatively constant by the fluid resistor technique as discussed above.

FIG. 6 is a simplified block diagram of the signal processing circuit to process the pulses of the particle sensing transducer 60 (FIG. 3) and which is claimed and disclosed in greater detail in the above copending Haynes/Shoor application. The output of particle sensing transducer 60 is amplified by ac amplifier 61 and has an output 62 connected to a base line restorer circuit 63. The output on line 62 is as illustrated in FIG. 6A the waveshape 62' where the large pulse is a red blood cell and the small pulse a platelet. The output of base line restorer circuit 63 restores the zero dc level as indicated on line 64 and waveform 64'. These particle pulses are then processed to count both red blood cells and platelets.

Specifically an upper threshold detector 66 separates platelets from red blood cells and a lower threshold detector 67 separates platelets from noise. The combination of these two detectors with a peak detector 68 allows the pulse sorter 69 to effectively count and separate out the red blood cell and platelet pulses. Thus, a platelet counter 71 counts the platelet pulses and a red blood cell counter 72 the RBC pulses. As indicated, RBC counter 72 is preset with the known density of the red blood cells of the sample of whole blood being taken by thumb wheel switches 8 (FIG. 1). As discussed in the Haynes/Shoor application if red blood cell density is known, then by taking the ratio of RBC counts and platelet counts, platelet density can be obtained. This is effectively done by the circuit of FIG. 6. However, platelet counter 71, by presetting the red blood cell density in RBC counter 72, will directly readout at 71' (FIG. 1) the platelet density when a stop signal is received in response to RBC counter 72 reaching the preset density count. Since this RBC count must be conducted in the same manner as the previous RBC count upper threshold detector 66 has its threshold set at a somewhat lower level than shown at 64' to include all particles having a size greater than 27.5 cubic microns. This is explained in greater detail in the copending Haynes/Shoor application.

In accordance with the present invention a total time test alarm circuit 73 is provided which is responsive to the start of the counting and its stopping. If the test time is less than 12 seconds or greater than 20 seconds a visual alarm 73a indicates a malfunction. Because of the accurate and stable dilution of the blood sample of 20,000:1 and the high repetitive test rate accomplished by the present invention, any test which is outside of the range of 12 to 20 seconds (or other equivalent range time) indicates a malfunction either in the electronic circuit, the fluid circuitry, that the sample is defective or that the preset known RBC density is incorrect. In addition, it might indicate the sample has some highly abnormal condition because of the number of particles or particle size.

In order to facilitate the high test sample rate capability of the present invention the base restorer circuit 63 as shown in greater detail in FIG. 6A is able to operate at a relatively high repetition rate. In general its purpose is to clamp the baseline of the ac coupled waveform produced by the ac amplifier circuit 61 to approximately zero volts dc thereby making it more convenient to discriminate pulses on the basis of their amplitude. The circuit of FIG. 6A includes a high pass filter circuit having a capacitor 102 and a PNP transistor 103 connected as an emitter follower. It is biased by resistors 104, 105 and 106 and has its emitter output to the noninverting input of an operational amplifier 107. This amplifier serves as a buffer. In operation the common collector configuration of transistor 103 provides a high input resistance to base current flowing toward the base-collector junction and a low resistance to base current flowing away from the junction toward capacitor 102. Thus the capacitor transistor combination provides a dc clamp to zero volts dc. The circuit also serves as a high pass filter eliminating 60 Hz ac current.

With the high sampling rate provided by the present invention, the Poisson sampling error which is $100/\sqrt{N}$ (expressed in %) is relatively low. However, in an aperture type counter as also shown by the curve of FIG. 7 labeled coincidence, as the sampling time increases the frequency of coincidence errors rises. The present invention compensates for this rise by the technique of ratioing the red blood cell count to the platelet count which inherently cancels out coincidence error.

Since platelets are discriminated from noise and red blood cells by their relative pulse heights, it is desirable that there be a relatively clear size valley between, for example, the largest platelets and the smallest red blood cells. The quality of this valley warns of abnormally small red blood cells, abnormally large platelets, or instrument malfunction. Also a second clear valley should occur between noise and the smallest platelet. This serves as a warning of excessive noise, abnormally small or deformed platelets, or instrument malfunction. Where such abnormal platelets are present a noise valley alarm may be an indication of pathological blood.

FIG. 8 is a whole blood cell distribution curve showing lower and upper valleys with the limits $V_1$ and $V_2$ for noise and the normal lower limit of platelet size. The limit $V_3$ is above the normal limit of the largest platelet and is less than the smallest red blood cell. In other words, $V_3$ and $V_4$ are conveniently chosen to provide a range where red blood cells or platelets do not normally occur. Moreover the above limits may be different from the threshold provided by detectors 66 and 67 (FIG. 6) since they are for alarm purposes only. It is obvious that all of the foregoing limits do not have rigid values. This is especially true of $V_1$ where the presence or absence of noise is very relative.

The circuits for implementing the foregoing are illustrated in FIGS. 9A and 9B where a peak hold circuit connected to baseline restorer 63 provides peak voltage $E_p$. A comparator 82 compares noise reference $V_1$ to the baseline input to peak hold circuit 81 to provide a strobe 1 pulse only when $E_p$ is greater than $V_1$. Strobe 1 is used in FIG. 9B to effectively provide a noise reference level.

An upper valley alarm circuit includes comparators 83 and 84 driving the AND gate 86 and NAND gate 87 which at its output 88 has a count of the upper valley pulses. These are counted by divide by $N_1$ unit 85, decimal counting units 89 and the sum supplied to a digital comparator 91.

A platelet count is provided through inverter 92, NAND gate 93 and counting units 94 which are also connected to comparator 91. If the valley count is greater than $N_1$% (e.g., 4% as provided by divider 85 where $N_1=4$) of the platelet count, upper valley alarm 96 is illuminated. Similarly, the lower valley pulses are provided by a comparator 97, NAND gate 98, divide by $N_2$ unit 95, and counting unit 99. A digital comparator 100 makes a similar comparison with the platelet count to illuminate lower valley alarm 101.

Thus, an improved method and apparatus for counting particles in a liquid suspension has been provided.

What is claimed is:

1. Apparatus for counting particles in a liquid suspension comprising: particle sensing means having a sensing aperture through which said particles pass; a vessel containing said liquid suspension; a source of particle free liquid; a small bore tube having one end immersed in said suspension and its other end juxtaposed with said aperture; means for forcing said suspension at a predetermined pressure through said tube and toward said aperture, said tube acting as a fluid resistor having a pressure drop across it such pressure drop being a significant fraction of said predetermined pressure; and hydrodynamic focusing means for directing a first flow of said particle free liquid through said aperture in cooperation with said liquid suspension said first flow being provided at substantially a pressure equal to said predetermined pressure minus said pressure drop.

2. Apparatus as in claim 1 where said vessel is closed and where said means for forcing said suspension at a predetermined pressure through said tube includes means for injecting a fluid under such pressure into said vessel and including means for allowing removal of said vessel from said apparatus to expose said one end of said tube to the ambient atmosphere whereby said first flow pressure causes said liquid suspension to back flow through said tube.

3. Apparatus for counting particles in a liquid suspension comprising: particle sensing means having a sensing zone through which said particles pass; a vessel containing said liquid suspension; a source of particle free liquid; a unitary small bore tube of uniform diameter having an end juxtaposed with said sensing zone; means for forcing said suspension at a predetermined pressure through said tube and into said sensing zone said tube acting as a fluid resistor having a pressure drop across it such pressure drop being a significant fraction of said predetermined pressure and hydrodynamic focusing means for directing a first flow of said particle free liquid through said sensing zone in cooperation with said liquid suspension said first flow being provided at substantially a pressure equal to said predetermined pressure minus said pressure drop.

4. Apparatus as in claim 3 including an outlet chamber for said liquid suspension having an opening juxtaposed with said sensing zone for receiving said suspension after passage through said sensing zone and means for directing a second flow of said particle free liquid to said opening of said outlet chamber to prevent eddy currents near said sensing zone.

5. Apparatus as in claim 3 where said sensing zone includes an aperture through which said particles pass.

6. Apparatus as in claim 2 where said predetermined fluid pressure is provided by a gas.

7. Apparatus for counting particles in a liquid suspension comprising: particle sensing means having a sensing zone through which said particles pass; a source of particle free liquid; a small bore tube having one end immersed in said suspension and its other end juxtaposed with said sensing zone; means for forcing said suspension at a predetermined pressure through said tube and into said sensing zone said tube acting as a fluid resistor having a pressure drop across it such pressure drop being a significant fraction of said predetermined pressure; and hydrodynamic focusing means for directing a first flow of said particle free liquid through said sensing zone in cooperation with said liquid suspension and including a fluid resistor for providing a pressure drop equal to said above pressure drop.

8. Apparatus for counting particles in a liquid suspension comprising particle sensing means having an aperture, an outlet chamber for said liquid suspension having an opening juxtaposed with said aperture for receiving said suspension after passage through said aperture; means for passing said liquid suspension through said aperture and toward said opening; a source of particle free liquid; hydrodynamic focusing means for directing a first flow of said particle free liquid through said aperture in cooperation with said liquid suspension; means for directing a second flow of said particle free liquid into said opening of said outlet chamber to prevent eddy currents near said aperture; said means for passing said liquid suspension through said aperture including a small bore tube having one end immersed in said suspension which is contained in a vessel and its other end juxtaposed with said aperture and means for forcing said suspension at a predetermined pressure through said tube said small bore tube having a pressure drop which is a significant fraction of said predetermined pressure.

9. Apparatus as in claim 8 where said tube acts as a fluid resistor having a pressure drop across it and said hydrodynamic focusing means provides said particle free liquid at substantially the said predetermined pressure minus said pressure drop.

10. Apparatus as in claim 9 where said hydrodynamic focusing means includes a fluid chamber for retaining said particle free liquid and a fluid resistor connecting said fluid chamber to said source of particle free fluid and having a pressure drop equal to said pressure drop of said small bore tube.

11. Apparatus as in claim 10 where said fluid resistor is a glass tube.

12. Apparatus as in claim 10 where said fluid resistor connecting said fluid chamber to said source of particle free liquid is fluidically in parallel with said small bore tube and has a substantially greater fluid flow rate than said tube to reduce sensitivity to pressure variations, and a common source of said predetermined pressure for said resistor and tube.

13. Apparatus as in claim 8 where said vessel is of a predetermined size having a sleeve-type opening and including means for injecting a gas into said vessel for providing said predetermined pressure including a collar surrounding a portion of said small bore tube and spaced therefrom said collar including an inlet aperture for said gas the exterior of said collar mating with said sleeve opening to close said vessel.

14. Apparatus as in claim 13 where said liquid suspension in said vessel is precisely diluted.

15. Apparatus as in claim 13 where said gas injection means includes means for limiting flow of said gas when said vessel is separated from said injection means.

16. Apparatus as in claim 8 where said source of particle free liquid is under said predetermined pressure.

17. Apparatus as in claim 16 where said vessel is closed and including means for injecting a gas into said vessel at said predetermined pressure for forcing said suspension through said tube and where said predetermined pressures of said source and said vessel are derived from a common gas source.

18. Apparatus as in claim 8 where said aperture is located at the apex of a cone said small bore tube extending substantially into said cone.

19. Apparatus as in claim 18 where said cone at its base includes a fluid inlet for said hydrodynamic focusing means connected to said source of particle free fluid.

20. Apparatus as in claim 19 where said cone at its base includes a fluid outlet for providing said second flow of particle free liquid.

21. Apparatus as in claim 20 together with a rectangular block of material having a central cylindrical cavity forming said outlet chamber at its upper portion but having an enlarged cross-section at its lower portion for retaining said cone, and first and second opposed adjacent cylindrical cavities intersecting said enlarged cross-section to allow said fluid inlet and outlet of said cone to respectively connect with said adjacent cavities.

22. Apparatus as in claim 21 where said cone includes a floor at its base through which said tube extends and said fluid inlet and outlet are juxtaposed whereby passage of fluid sweeps said floor clean of debris.

23. Apparatus as in claim 8 where said outlet chamber, hydrodynamic focusing means, sensing means, and means for directing said second flow are all formed, at least in a substantial part, in a block of transparent material whereby the user can view all fluid paths.

24. Apparatus as in claim 8 where said outlet chamber opening is relatively small and in close proximity to said aperture for providing a high velocity but low volume flow.

25. Apparatus as in claim 21 together with a cylindrical holder removably inserted in said enlarged cross-section and including said cone and aperture.

26. Apparatus as in claim 21 where said particle sensing means includes a pair of electrodes with one of said electrode pair extending into said cavity associated with said fluid outlet.

27. Apparatus as in claim 26 where said other electrode of said pair is located in said outlet chamber and both electrodes are exclusively constructed of wire of a predetermined diameter.

28. Apparatus as in claim 8 together with means for metering said flow of particle free liquid for sensing malfunctions in said apparatus.

29. Apparatus for counting particles in a liquid suspension comprising particle sensing means having an aperture; an outlet chamber having an opening juxtaposed with said aperture; means for passing said liquid suspension through said aperture and toward said opening; a source of particle free liquid; hydrodynamic focusing means including a fluid chamber connected to said source of particle free liquid for directing a first flow of said particle free liquid through said aperture in cooperation with said liquid suspension; means for directing a second flow of said particle free liquid into said opening of said outlet chamber; a fluid resistor connecting said fluid chamber to said second flow directing means said fluid chamber providing substantially all of said fluid for such means.

30. Apparatus as in claim 29 together with filter means in series with said source of particle free liquid and said fluid chamber for removing small bubbles which otherwise could be mistaken as a particle in said suspension.

31. Apparatus as in claim 29 where said fluid resistor is a glass tube.

32. Apparatus as in claim 29 where said fluid chamber serves as a settling chamber for removing bubbles.

33. Apparatus as in claim 29 where said fluid resistor has an inner diameter to provide a fluid flow with a high electrical resistance relative to said aperture.

34. Apparatus for counting particles in a liquid suspension comprising: particle sensing means having a sensing zone through which said particles pass; a closed vessel containing a liquid suspension; a source of particle free liquid; a small bore tube having one end immersed in said suspension and its other end juxtaposed with said zone; means for injecting a fluid under a predetermined pressure into said vessel for forcing said suspension through said tube and toward said sensing zone said small bore tube having a pressure drop which is a significant fraction of said predetermined pressure, means for directing under pressure a flow of said particle free liquid through said zone in cooperation with said liquid suspension; and means for allowing removal of said vessel from said apparatus to expose said one end of said tube to the ambient atmosphere where said pressure of said particle free liquid causes said liquid suspension to back flow through said tube.

* * * * *